United States Patent [19]
Bloom et al.
[11] 3,944,569
[45] Mar. 16, 1976

[54] AMINOMETHYL-SUBSTITUTED 1-NAPHTHOL PHTHALIDES AND NAPHTHALIDES

[75] Inventors: Stanley M. Bloom, Waban; Elbert M. Idelson, Newton Lower Falls; Myron S. Simon, West Newton; David P. Waller, Arlington, all of Mass.

[73] Assignee: Polaroid Corporation, Cambridge, Mass.

[22] Filed: Aug. 27, 1973

[21] Appl. No.: 392,104

Related U.S. Application Data

[62] Division of Ser. No. 177,497, Sept. 2, 1971, Pat. No. 3,779,753.

[52] U.S. Cl. ................ 260/343.3 R; 260/326.14 R; 260/343.2 R
[51] Int. Cl.[2] .................................... C07D 307/77
[58] Field of Search ........ 260/343.3, 343.4, 343.2 R

[56] References Cited

UNITED STATES PATENTS

| | | | |
|---|---|---|---|
| 499,927 | 6/1893 | Monnet | 260/343.4 |
| 3,301,870 | 1/1967 | Terzijska et al. | 260/343.4 |

*Primary Examiner*—Donald G. Daus
*Assistant Examiner*—Anne Marie T. Tighe
*Attorney, Agent, or Firm*—Sybil A. Campell

[57] ABSTRACT

This invention relates to a class of phthalein indicator dyes useful as optical filter agents in photographic processes to protect a selectively exposed photosensitive material from further exposure during processing in the presence of incident light. Such dyes comprise 3,3-disubstituted phthalides and 3,3-disubstituted naphthalides wherein the 3,3 substituents are p-hydroxy carbocyclic aryl radicals wherein one or both of the radicals possess a $-CH_2-NRR'$ group ortho to the p-hydroxy group and the $-CH_2-NRR'$ group(s) is capable of rendering the indicator dye substantially non-diffusible in aqueous solution.

21 Claims, No Drawings

AMINOMETHYL-SUBSTITUTED 1-NAPHTHOL PHTHALIDES AND NAPHTHALIDES

Cross Reference to Related Applications

This application is a division of application Ser. No. 177,497 filed Sept. 2, 1971, now U.S. Pat. No. 3,779,753.

BACKGROUND OF THE INVENTION

1. Field of the Invention

The present invention relates to novel chemical compounds, and more specifically, it relates to a new class of phthalein indicator dyes. In a particular aspect it relates to certain phthaleins useful as optical filter agents in photographic processes for protecting an exposed photosensitive material from post-exposure fogging during development in the presence of extraneous incident light and to such photographic uses.

2. Description of the Prior Art

A number of photographic processes by which images may be developed and viewed within seconds or minutes after exposure have been proposed. Such processes generally employ a processing composition which is suitably distributed between two sheet-like elements, the desired image being carried by one of said sheet-like elements. The resulting images may be in black-and-white, e.g., in silver, or in one or more colors. Processing may be conducted in or outside of a camera. The most useful of such processes are the diffusion transfer processes which have been proposed for forming silver or dye images, and several of these processes have been commercialized. Such processes have in common the feature that the final image is a function of the formation of an image-wise distribution of an image-providing reagent and the diffusion transfer of said distribution to or from the stratum carrying the final image, whether positive or negative.

U.S. Pat. No. 3,415,644 discloses a composite photosensitive structure, particularly adapted for use in reflection type photographic diffusion transfer color processes. This structure comprises a plurality of essential layers including, in sequence, a dimensionally stable opaque layer; one or more silver halide emulsion layers having associated therewith dye image-providing material which is soluble and diffusible, in alkali, at a first pH, as a function of the point-to-point degree of its associated silver halide emulsion's exposure to incident actinic radiation; a polymeric layer adapted to receive solubilized dye image-providing material diffusing thereto; a polymeric layer containing sufficient acidifying capacity to effect reduction of a processing composition from the first pH to a second pH at which the dye image-providing material is substantially nondiffusible; and a dimensionally stable transparent layer. This structure may be exposed to incident actinic radiation and processed by interposing, intermediate the silver halide emulsion layer and the reception layer, an alkaline processing composition providing the first pH and containing a light-reflecting agent, for example, titanium dioxide to provide a white background. The light reflecting agent (referred to in said patent as an "opacifying agent") also performs an opacifying function, i.e., it is effective to mask the developed silver halide emulsions and also acts to protect the photoexposed emulsions from postexposure fogging by light passing through the transparent layer if the photoexposed film unit is removed from the camera before image formation is complete.

In a preferred embodiment, the composite photosensitive structure includes a rupturable container, retaining the alkaline processing composition having the first pH and light-reflecting agent, fixedly positioned extending transverse a leading edge of the composite structure in order to effect, upon application of compressive pressure to the container, discharge of the processing composition intermediate the opposed surfaces of the reception layer and the next adjacent silver halide emulsion.

The liquid processing composition distributed intermediate the reception layer and the silver halide emulsion, permeates the silver halide emulsion layers of the composite photosensitive structure to initiate development of the latent images contained therein resultant from photoexposure. As a consequence of the development of the latent images, dye image-providing material associated with each of the respective silver halide emulsion layers is individually immobilized as a function of the point-to-point degree of the respective silver halide emulsion layer photoexposure, resulting in imagewise distributions of mobile dye image-providing materials adapted to transfer, by diffusion, to the reception layer to provide the desired transfer dye image. Subsequent to substantial dye image formation in the reception layer, a sufficient portion of the ions of the alkaline processing composition transfers, by diffusion, to the polymeric neutralizing layer to effect reduction in the alkalinity of the composite film unit to the second pH at which dye image-providing material is substantially nondiffusible, and further dye image-providing material transfer is thereby substantially obviated.

The transfer dye image is viewed, as a reflection image, through the dimensionally stable transparent layer against the background provided by the reflecting agent, distributed as a component of the processing composition, intermediate the reception layer and next adjacent silver halide emulsion layer. The thus-formed stratum effectively masks residual dye image-providing material retained in association with the developed silver halide emulsion layer subsequent to processing.

In the copending U.S. patent application Ser. No. 786,352 of Edwin H. Land, filed Dec. 23, 1968, now abandoned and Ser. No. 101,968 filed Dec. 28, 1970, now U.S. Pat. No. 3,647,437 in part a continuation of Ser. No. 786,352, an organic light-absorbing reagent (or optical filter agent), such as a dye, which is present as a light-absorbing species at the first pH and which may be converted to a substantially non-light-absorbing species at the second pH is used in conjunction with the light-reflecting agent to protect the selectively exposed silver halide emulsions from post-exposure fogging when development of the photoexposed emulsions is conducted in the presence of extraneous incident actinic radiation impinging on the transparent layer of the film unit.

In the processes of aforementioned applications Ser. Nos. 785,352, now abandoned, and 101,968, now U.S. Pat. No. 3,647,437, and in other photographic processes, it is preferred to use, as the optical filter agent, a dye that is substantially non-diffusible in the photographic processing composition in order to achieve optimum efficiency as a radiation filter and to prevent diffusion of optical filter agent into layers of the film unit where its presence may be undesirable. The present invention is concerned with pH-sensitive dyes, namely, certain phthaleins of hydroxy-substituted carbocyclic aryl compounds, i.e., phenols and 1-naphthols, useful as optical filter agents that are substantially non-diffusible in aqueous solution.

SUMMARY OF THE INVENTION

It is therefore the primary object of the present invention to provide novel indicator dyes.

It is a further object of the present invention to provide phenol and 1-naphthol phthalein indicator dyes useful as optical filter agents in photographic processes for preventing post-exposure fogging of a selectively exposed photosensitive material during development in the presence of incident light.

It is a further object of the present invention to provide products, compositions and processes for the development of photosensitive materials in which the novel phthalein indicator dyes are used.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

According to the present invention, there is provided a novel class of indicator dyes selected from 3,3-disubstituted phthalides and 3,3-disubstituted naphthalides wherein the 3,3 substituents are p-hydroxycarbocyclic aryl radicals, one or both of said radicals possessing a $-CH_2-NRR'$ group ortho to the para-hydroxy group, said $-CH_2-NRR'$ group or groups being capable of rendering the dye substantially non-diffusible in aqueous solution. These dyes will be defined with greater particularity hereinafter.

Like phthalein dyes, generally, the dyes of the present invention exhibit reversibly alterable spectral absorption characteristics in response to changes in environmental pH. They have a colored, light-absorbing form in alkaline media at a first pH value above their pKa and a substantially colorless form, i.e., a form which is substantially non-light-absorbing in the visible spectrum at a second pH below their pKa. By pKa is meant the pH at which about 50% of the dye is present in its light-absorbing form and about 50% is present in its non-light-absorbing form.

It will be appreciated that such compounds will find utility in titrations and other analytical procedures where phthalein indicator dyes are commonly employed, for example, to measure changes in pH value as reflected by the change in color of the dye from one color to another or from colored to colorless or vice versa. The indicator dyes of the present invention, however, because they are substantially non-diffusible in aqueous media and because of certain other properties, are especially useful as optical filter agents in photographic processes where development of a selectively exposed photosensitive material is performed at least in part outside the confines of a camera in the presence of extraneous incident actinic radiation.

For a fuller understanding of the nature and objects of the present invention, reference should be had to the following detailed description.

DESCRIPTION OF THE PREFERRED EMBODIMENTS

According to the present invention, it has been found that phenol and 1-naphthol phthaleins which are substantially non-diffusible in aqueous media may be obtained by condensing the phthalein dye or dye-intermediate, with formaldehyde and a primary or secondary amine to introduce a suitable "anchor" or "immobilizing" $-CH_2-NRR'$ group into the 2-position of the p-hydroxyphenyl or p-hydroxynaphthyl radical(s), i.e., ortho to the functional hydroxy group. It also has been found that a substantial increase in pKa results when both the R and R' substituents of the $-CH_2-NRR'$ group are other than hydrogen. Because of the higher pKa, the dye may be rendered colorless at a higher pH in aqueous alkaline processing media. Thus, upon pH reduction, they may be cleared more rapidly than simple phenol and naphthol phthaleins in photographic processes where it is desired to view image formation soon after the initial stages of development.

As noted above, the novel indicator dyes of the present invention comprise two p-hydroxycarbocyclic aryl radicals bonded to a phthalide or naphthalide ring-closing moiety, one or both, and preferably, both of the carbocyclic aryl radicals being substituted ortho to the p-hydroxy group with a $-CH_2-NRR'$ group. When both radicals are so substituted, the $-CH_2-NRR'$ groups may be the same or different, and preferably, are the same. The p-hydroxycarbocyclic aryl radicals are selected from two p-hydroxyphenyl radicals and two p-hydroxynaphthyl radicals. Typical of the indicator dyes of the present invention are those represented by the formula:

(I)

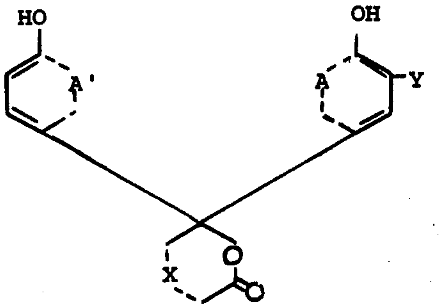

wherein A and A', the same, represent the carbon atoms necessary to complete a radical selected from phenyl and naphthyl; Y represents the group $-CH_2-NRR'$ wherein R is hydrogen, alkyl, aryl or acyl and R' is alkyl, aryl or alkaryl; and X represents the atoms necessary to complete a ring-closing moiety selected from a phthalide and a naphthalide. Preferably, the A' radical contains an ortho substituent Y', i.e.,

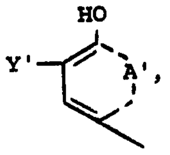

wherein Y' represents the group $-CH_2-NRR'$ and said R and said R' both have the same meaning given above.

Examples of substituents that may comprise R and R' are branched and preferably straight chain alkyl groups, such as, methyl, ethyl, propyl, butyl, hexyl, octyl, nonyl, decyl, dodecyl, hexadecyl, octadecyl, and eicosanyl; aryl groups, such as, phenyl, and naphthyl; and alkaryl groups, such as, phenyldecyl, phenyloctyl, phenylhexyl, p-octylphenyl and p-dodecylphenyl. Examples of acyl substituents are those of the formula

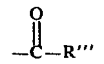

wherein R''' is alkyl, aryl, or alkaryl, such as, the respective groups enumerated above.

Since the $—CH_2—NRR'$ group or groups should render a given dye substantially non-diffusible in a given aqueous solution, the respective R' substituent(s) will be selected so that together with the respective R substituent(s), the resulting dye is substantially immobile in solution. For example, when the R substituent(s) is hydrogen, relatively long chain alkyl groups, such as, dodecyl or octadecyl may be selected as the R' substituent(s), whereas an alkyl group with a lesser number of carbon atoms may be adequate to achieve substantial non-diffusibility of the dye where the R substituent(s) is a relatively long chain group(s).

The indicator dyes defined above and as represented in the foregoing formula may contain substituents other than those specified on the p-hydroxycarbocyclic aryl radicals and/or the ring-closing moiety. Typical substituents include alkyl, such as, methyl, ethyl, propyl; alkoxy, such as, methoxy, ethoxy, butoxy; halo, such as, fluoro, chloro, bromo; and solubilizing groups as exemplified by hydroxy, carboxy and sulfo. It will bee recognized, however, that such additional substituents should not interfere with the function of the dye for its intended ultimate use and also that substituents, such as, the solubilizing or other groups may be included in the $—CH_2—NRR'$ group(s) rather than being substituted directly on the carbocyclic radicals and/or the ring-closing moiety. Preferably, the dyes of the present invention are symmetrical, i.e., bis phthalides and naphthalides wherein the two phenyl or the two naphthyl radicals contain the same substituents in the same positions so that they are identical.

Specific examples of indicator dyes within the scope of the present invention are as follows (1)

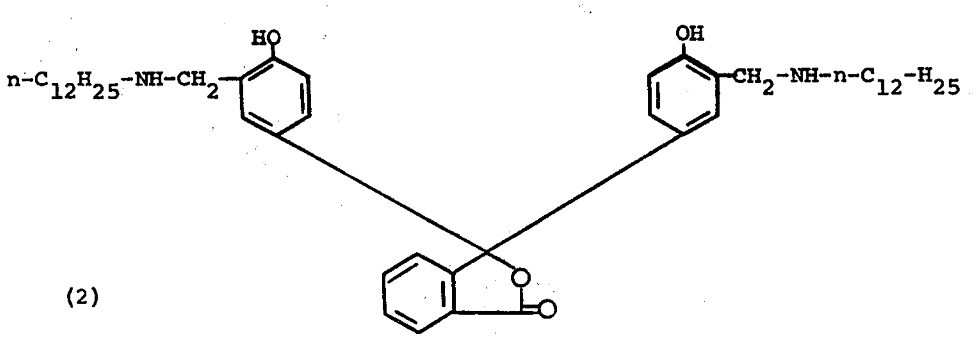

(2)

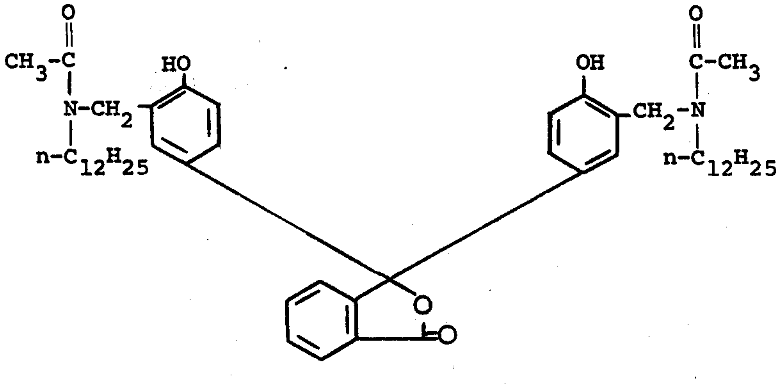

(3)

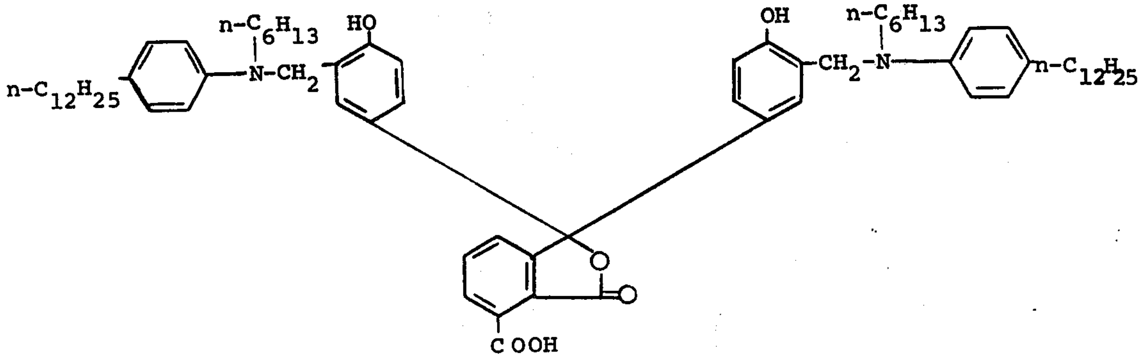

(4)
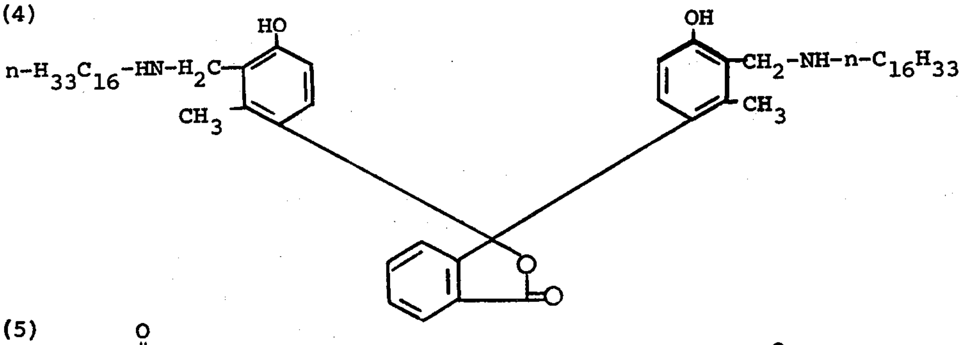
(5)
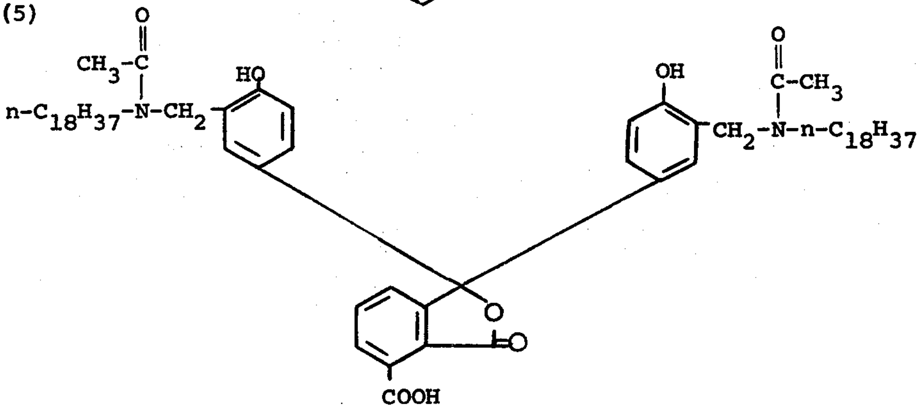
(6)
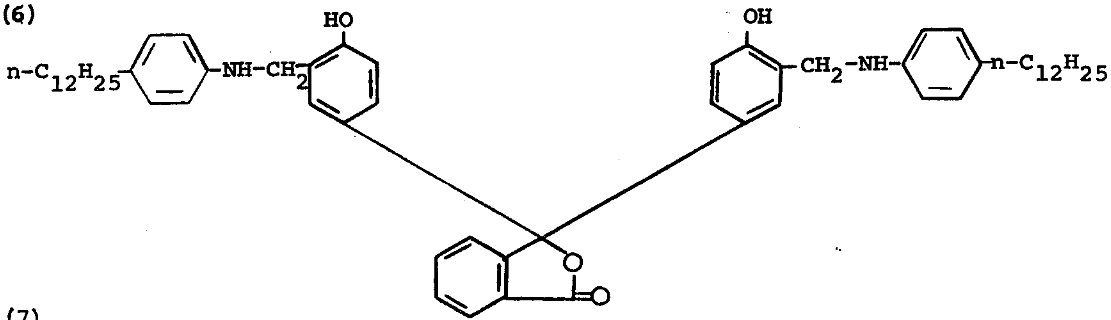
(7)
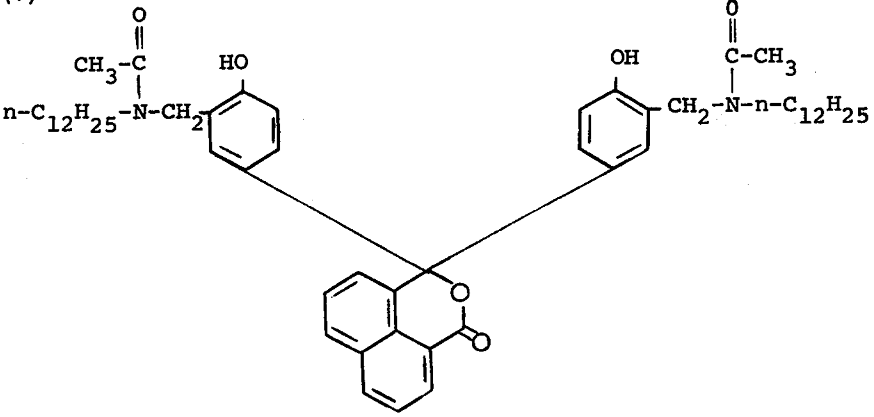
(8)
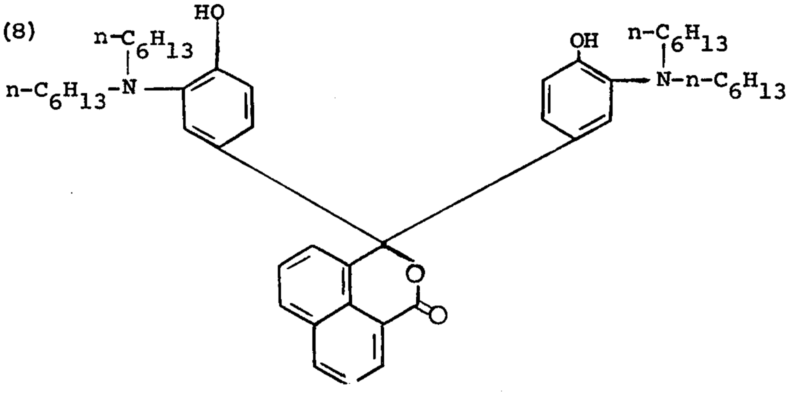

(9)
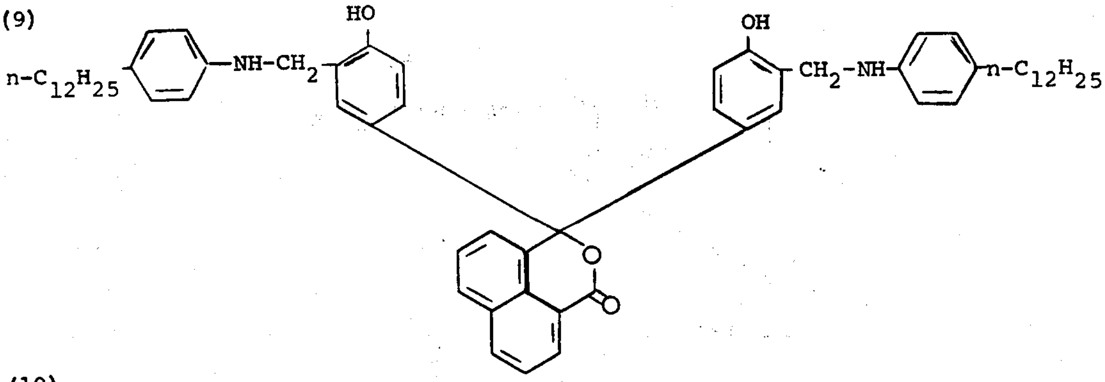
(10)
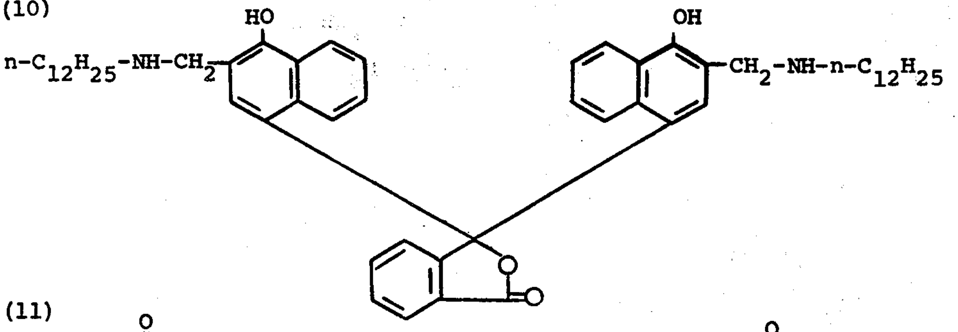
(11)
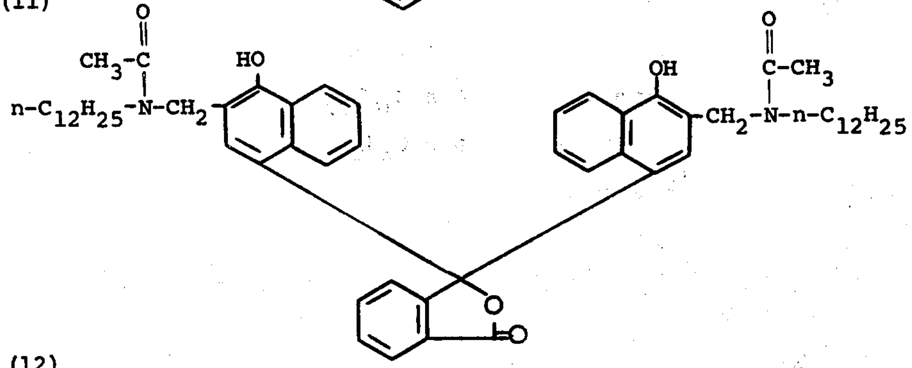
(12)
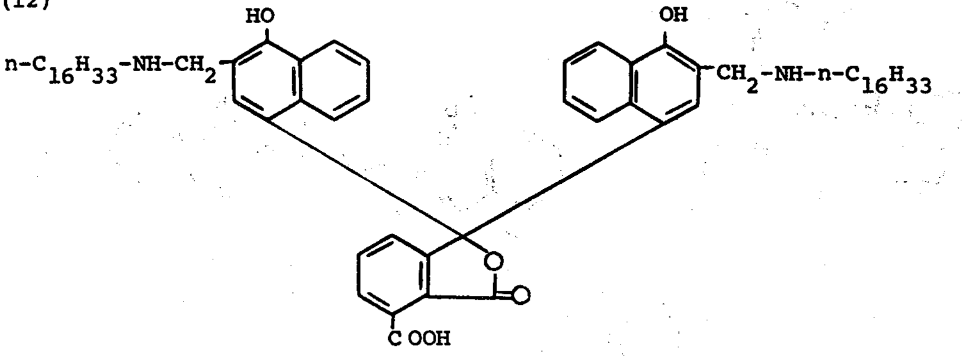
(13)
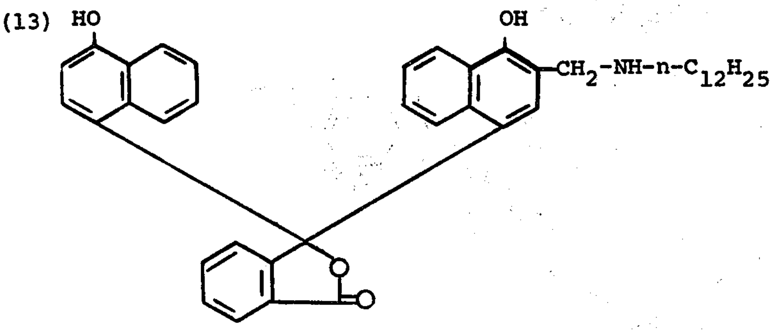

(14)
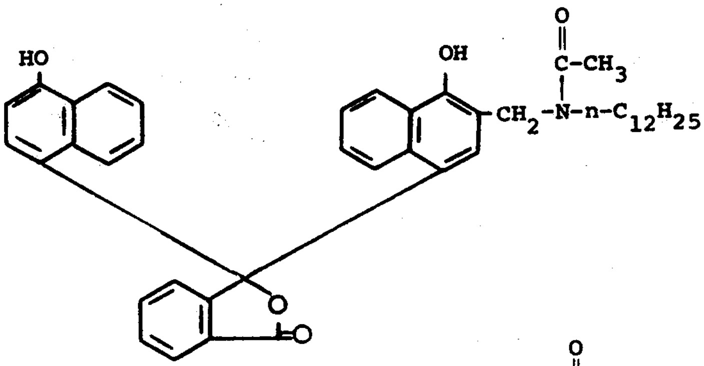
(15)
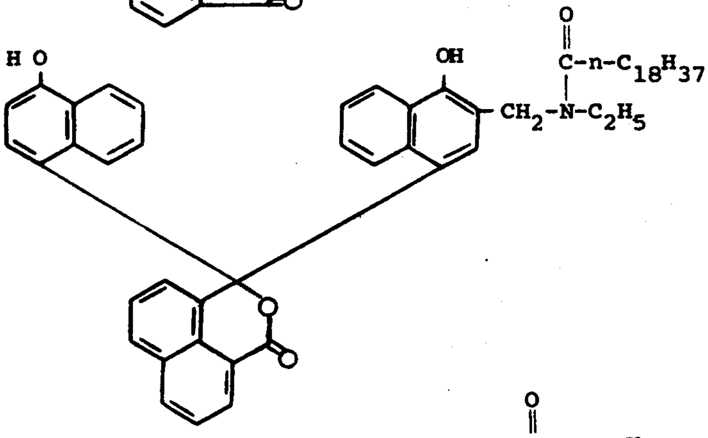
(16)
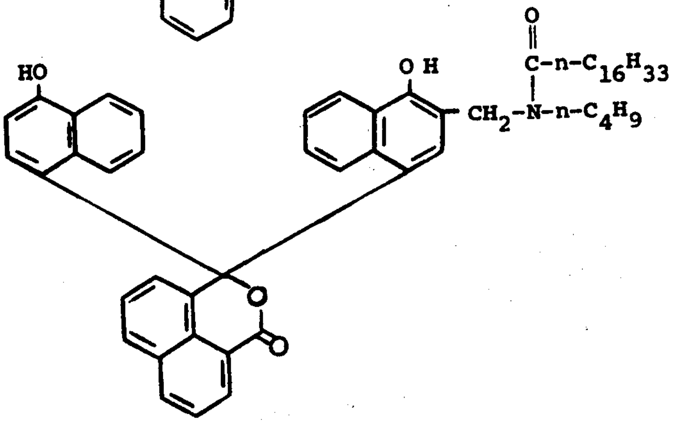
(17)
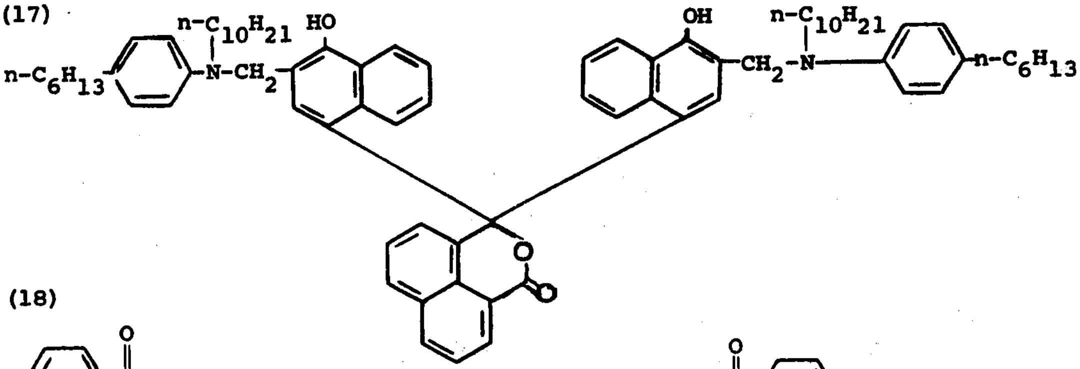
(18)
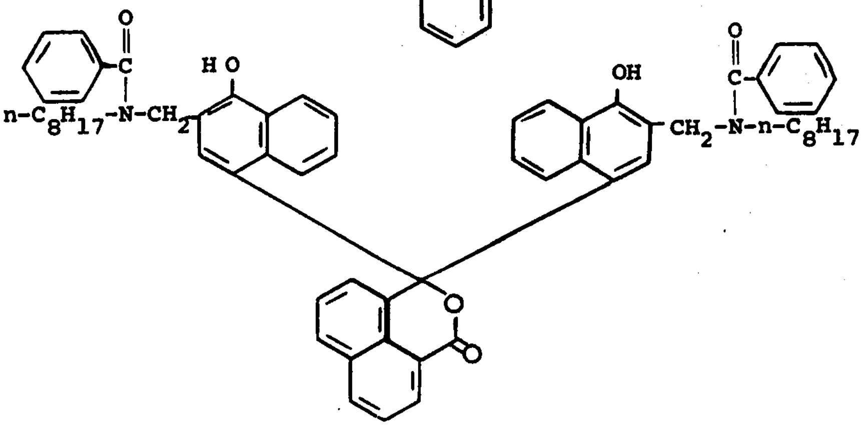

(19)
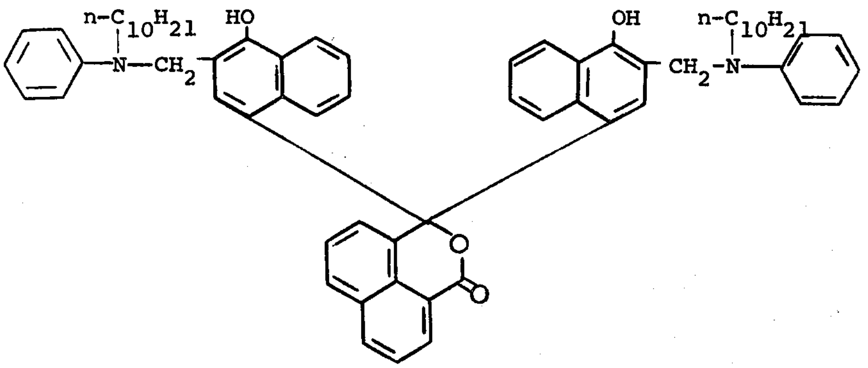
(20)
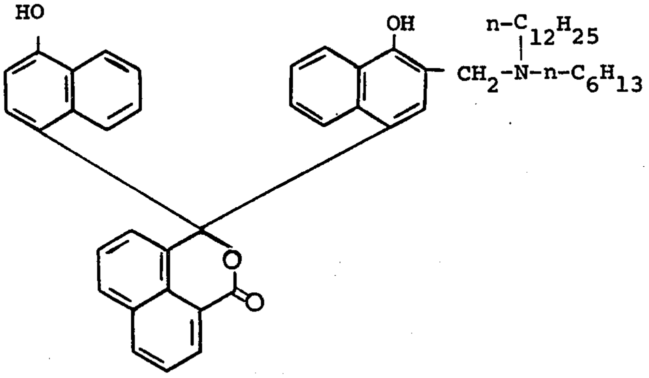
(21)
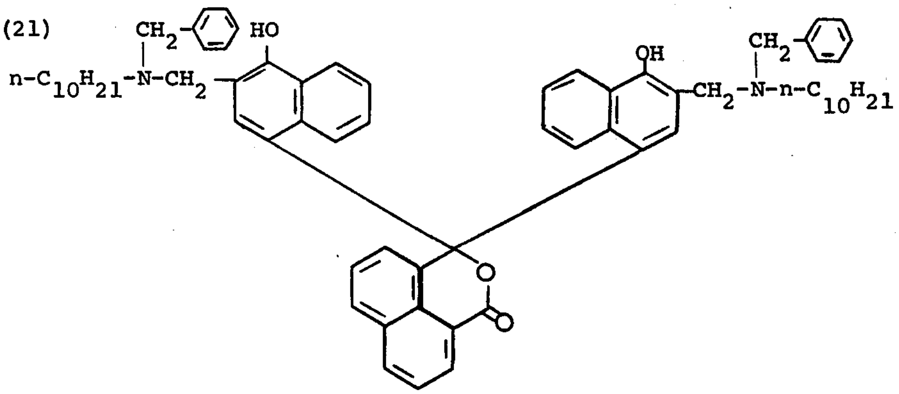
(22)
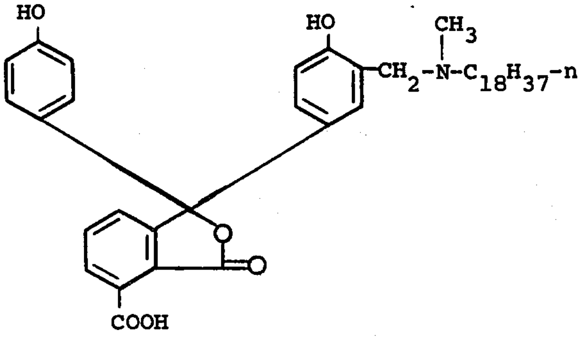
(23)
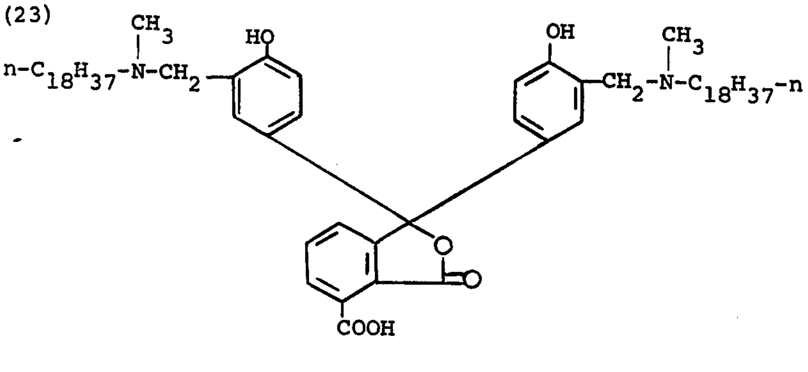

In preparing the dyes of the present invention, the $—CH_2—NRR'$ group or groups may be introduced by reacting a dye intermediate and/or a phthalide or naphthalide indicator dye with formaldehyde and a primary or secondary amine. For example, a dye intermediate, such as, 3-hydroxy-3-(4'-hydroxynaphthyl) naphthalide-1,8 may be condensed with formaldehyde and the appropriate amine to yield the corresponding (3'$-CH_2$—NRR'—4'—hydroxynaphthyl) naphthalide intermediate. This intermediate may then be reacted with a 1-naphthol under Friedel Crafts conditions to yield the complete dye. The naphthol reacted with the dye intermediate may contain a $—CH_2—NRR'$ group or this group may be introduced subsequent to forming the complete dye by reacting the complete dye with formaldehyde and amine. Where the R substituent or the methylamino group(s) is hydrogen, the dye intermediate or the complete dye may be reacted with an acylating agent, e.g., acetyl chloride to convert the amino to amido group(s). By employing the foregoing procedure, phenol and 1-naphthol phthalides and naphthalides may be prepared which contain one or two $—CH_2—NRR'$ groups, the same or different.

As noted above, the indicator dyes of the present invention are preferably symmetrical. Both phenol and both naphthol radicals contain the same substituents in the same positions including identical $—CH_2—NRR'$ groups. Such dyes may be prepared more conveniently by simply reacting a phenol or 1-naphthol phthalide or naphthalide with formaldehyde and an amine and then treating product with an acylating agent where appropriate and desired to produce the amido group.

It will be appreciated that the phenol or 1-naphthol radical(s) of the phthalein dye or dye intermediate employed as the starting material should have a free 2-position, i.e., a free position ortho to the p-hydroxy group for the condensation reaction with formaldehyde and the amine. The amine used may be any primary amine that will provide the desired R' substituent described above or any secondary amine that will provide the desired R and R' substituents. Where the methylamino groups are subsequently acylated, any of the agents commonly used in acylation reactions may be employed. Both the condensation reaction and acylation reaction may be carried out in a conventional manner.

The following Examples are given to further illustrate the present invention and are not intended to limit the scope thereof.

EXAMPLE 1

Preparation of the compound of formula (10)

Analytical grade 1-naphtholphthalein.$2CHCl_3$ (2 equivalents) was dissolved in ethanol (1g./5ml.) in a 3-neck round-bottom flask fitted with mechanical stirrer, thermometer, and dropping funnel. n-Dodecyl amine (5 equivalents) was dissolved in ethanol (1g./10ml.) and added in one portion to the reaction vessel. To this well-stirred solution, formalin (containing 2.1 equivalents formaldehyde) in ethanol (1 ml./5ml.) was added dropwise over 1 hour at a rate such that the temperature of the reaction mixture did not exceed 30°C. and the mixture stirred at room temperature about 14 hours. The reaction mixture was filtered and washed with ethanol into a round-bottom flask and evaporated on a rotary evaporator with the heating bath maintained at <30°C. The residual dark paste was triturated with excess hexane (approximately 1 g./40ml..) until an easily filterable solid was obtained. The solid was collected and triturated again with hexane, collected and washed well with hexane to ensure that all unconverted dodecylamine had been removed. An analytical sample was obtained by crystallization from boiling hexane. The bulk of the crude sample was dissolved in hot chloroform (1g./5ml.), filtered, and diluted with 10 volumes hexane and allowed to stand several hours. The title compound was recovered in about 70–80% by weight.

EXAMPLE 2

Preparation of the compound of formula (11)

The product obtained in Example 1 above was dissolved in dry pyridine (1g./10ml.) in a flame-dried round-bottom flask fitted with a dropping funnel to give an intense sienna solution which was chilled in an ice bath to about 5°C. Acetyl chloride (10 equivalents) was added dropwise. After a short time a solid separated and the reaction mixture turned bright yellow. When addition was complete, the cooling bath was removed and the reaction mixture allowed to come to room temperature. The reaction mixture was poured into dilute hydrochloric acid; the off-white solid was triturated, collected, washed thoroughly with dilute hydrochloric acid, and dried to give a pale yellow solid.

The crude tetraacetate was dissolved in methanol (1g./40ml.) and filtered. Dilute alkali was added, and the reaction mixture was stirred 1 hour at room temperature. The intensely blue solution was filtered to remove minor amounts of insoluble materials and the filtrate precipitated into dilute hydrochloric acid. The precipitate was collected, washed and dried and recrystallized from ethyl acetate/hexane to yield the title compound.

EXAMPLE 3

Preparation of the compound of formula (14)

Following the procedure of Example 1, 3-hydroxy-3-(4'-hydroxynaphthyl)phthalide was reacted with n-dodecylamine and formalin and then acetylated according to the procedure of Example 2. The intermediate thus obtained was treated with aqueous sodium hydroxide and then reacted with an equivalent of 1-naphthol in the presence of phosphorus oxychloride to yield the title compound.

EXAMPLE 4

Preparation of the compound of Formula (1)

Following the procedure of Example 1, analytical grade phenol phthalein was reacted with formalin and n-dodecylamine to yield the title compound.

Each of the indicator dyes prepared in the above examples was coated in a layer of gelatin over another layer comprising gelatin carried on a support. This element was then superposed with a second element comprising a polymeric layer of polyvinyl alcohol and poly-4-vinylpyridine carried on a transparent support. An aqueous alkaline solution having a pH in excess of about 12 and comprising water, potassium hydroxide and titanium dioxide was spread between the superposed elements. Optical density was measured over a period of about 2 minutes through the transparent support of the second element commencing upon spreading of the aqueous solution to determine whether or not indicator dye was migrating through the layer of aqueous solution to the polymeric layer. The density measurements as measured by reflection at the $\lambda_{max}$ for each dye revealed that substantially no increase in density occurred during the 2 minute interval indicating that each of the dyes was substantially non-diffusible from its original position in the first element.

As noted above, it has been found that the pKa of the indicator dyes containing $-CH_2-NRR'$ group(s) wherein R is other than hydrogen, e.g., acetyl, exhibit a higher pKa than those dyes where the R substituent is hydrogen. For example, the pKa value measured for the indicator dye of Example 1 was approximately 7 which is in substantially the same range as the pKa for 1-naphtholphthalein which has two pKa's, one at about 7 and a second at about 8. In comparison, the pKa values measured for the indicator dyes of Examples 2 and 3 were 10.1 and 9.2, respectively. Because of the substantial increase in pKa for dyes of the latter type, such dyes may be rendered colorless at a high pH. Such dyes are particularly useful as optical filter agents in photographic processes, e.g., diffusion transfer processes performed at a comparatively high pH where it is desired to clear the dye relatively rapidly upon reduction of the pH to permit early viewing of the image.

The pH sensitive indicator dyes of the present invention may be used as optical filter agents in any photographic process including conventional tray processing and diffusion transfer photographic techniques. In such processes, the dye or dyes during development of a selectively exposed photosensitive material will be in a position and in a concentration effective to absorb a given level of non-selective radiation incident on and actinic to the photosensitive material. The dyes may be initially disposed in the film unit, for example, in a layer(s) coextensive with one or both surfaces of the photosensitive layer. Where selective exposure of the photosensitive material is made through a layer containing the indicator dye, then the dyes should be in a non-light-absorbing form until the processing solution is applied. Alternately, the dyes may be initially disposed in the processing composition in their light-absorbing form, for example, in the developing bath in tray processing or in the layer of processing solution distributed between the photosensitive elemtn and the superposed image-receiving element (or spreader sheet) in diffusion transfer processing. The particular indicator dye or dyes selected should have an absorption spectrum corresponding to the sensitivity of the photosensitive layer, so as to afford protection over the predetermined wavelength range required by the particular photosensitive material employed and should have a pka such that they are in their colored form, i.e., light-absorbing form at the pH at which the photographic process is performed. Most commercially useful photographic processes are performed under alkaline conditions. Diffusion transfer processes, for example, usually employ highly alkaline processing solutions having a pH in excess of 12.

In photographic processes where the optical filter agent is retained in a stratum through which the final image is to be viewed, the color of the indicator dye may be discharged subsequent to image formation by adjusting the pH of the system to a value at which the dye is substantially non-light absorbing in the visible spectrum. In photographic processes performed at an alkaline pH, the optical filter agent, such as, a dye or dyes of the present invention are rendered substantially colorless by reducing the environmental pH. In processes where the optical filter agent is removed or separated from the layer containing the final image or retained in a layer that does not interfere with viewing of the final image, it is unnecessary to convert the indicator dye to its non-light-absorbing form, though the color may be discharged if desired.

The concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. It has been found, by interposing neutral density (carbon containing) filters over a layer of titanium dioxide, that a transmission density of approximately 6.0 from said neutral density filters was effective to prevent fogging of a diffusion transfer multicolor film unit of the type described in said U.S. Pat. No. 3,415,644 having a transparent support layer and an Equivalent ASA Exposure Index of approximately 75, when processed for one minute in 10,000 foot candles of color corrected light, a light intensity approximating the intensity of a noon summer sun. The transmission density required to protect such a film unit under the stated conditions may also be expressed in terms of the "system" transmission density of all the layers intermediate the silver halide layer(s) and the incident light; the "system" transmission density required to protect color film units of the aforementioned type and photographic speed has been found to be on the order of 7.0 to 7.2. Lesser levels of optical transmission density would, of course, provide effective protection for shorter processing times, lesser light intensities and/or films having lower exposure indices. The transmission density and the indicator dye concentration necessary to provide the requisite protection from incident light may be readily determined for any photographic process by following the above described procedure or obvious modifications thereof.

Since most commercial photographic processes employ photosensitive materials sensitive to and exposable by actinic radiation throughout the visible spectrum, e.g., black-and-white panchromatic silver halide emulsions and multilayer silver halide emulsion elements, it is preferred to use a second dye(s) in conjunction with the subject dye(s) that has a principal absorption in a second and at least partially different predetermined wavelength range such that the combination of dyes will afford protection from non-selective incident actinic radiation over the range of 400 to 700 nm. The second dye employed may be non-color-changing but preferably, is also pH sensitive, i.e., has reversibly alterable spectral absorption characteristics in response to changes in the environmental pH so that it may be rendered light-absorbing or non-light-absorbing as desired. Illustrative of such dyes are phthaleins derived from indoles, such as, indole phthalein. The second dye also may be initially present in the film unit or in the processing composition as discussed above either together with or separate from the subject dyes and subsequent to processing may be removed from the film unit or retained within the film structure, provided it is in a form or position such that it does not interfere with viewing of the image produced.

Dyes may be selected from those described above that are particularly useful as optical filter agents in diffusion transfer processes, for example, those employing composite diffusion transfer photosensitive elements including a film pack or roll wherein superposed photosensitive and image-receiving elements are maintained as a laminate after formation of the final image. Such elements include at least one transparent support to allow viewing of the final image without destroying the structural integrity of the film unit. Preferably, the support carrying the photosensitive layer(s) is opaque and the support carrying the image-receiving layer is transparent and selective photoexposure of the photosensitive layer(s) and viewing of the final image both are effected through the latter support. The final image is viewed as a reflection print, i.e., by reflected light, provided by a reflecting agent initially disposed in the processing composition applied and maintained intermediate the image-receiving and next adjacent photosensitive layer or by a preformed layer of reflecting agent initially positioned intermediate the image-receiving and next adjacent photosensitive layer. It will be understood that a preformed reflecting layer, while it should be capable of masking the photosensitive layer(s) subsequent to image formation, should not interfere with selective photoexposure of the photosensitive material prior to processing.

When utilizing reflection-type composite film units, the indicator dye or dyes employed as the optical filter agent(s) may be positioned initially in a layer of the film unit, e.g., in a layer between the image-receiving and next adjacent photosensitive layer through which photoexposure is effected provided it is incorporated under conditions, i.e., at a pH such that it will not absorb actinic radiation intended to selectively expose the photosensitive material to form a latent image therein. For example, the optical filter agent may be in a layer coated over either the image-receiving layer or the next adjacent photosensitive layer and should remain substantially non-light-absorbing until a processing composition is applied provided a pH at which the indicator dye is capable of being rapidly converted to its light-absorbing form to provide light protection when the film unit is removed from the camera. Rather than being initially disposed in the film unit, the indicator dye may be initially present in the processing composition applied intermediate the image-receiving and next adjacent photosensitive layer subsequent to photoexposure. The dye, when initially disposed in the processing composition, will be in its light-absorbing form.

The dyes selected as optical filter agents should exhibit at the initial pH of the processing, maximum spectral absorption of radiation at the wavelengths to which the film unit's photosensitive silver halide layer or layers are sensitive, and preferably, should be substantially immobile or nondiffusible in the alkaline processing composition in order to achieve optimum efficiency as a radiation filter and to prevent diffusion of filter agent into layers of the film unit where its presence may be undesirable. Recognizing that the filter agent absorption will detract from image-viewing characteristics by contaminating reflecting pigment background, the selected agents should be those exhibiting major spectral absorption at the pH at which processing is effected and minimal absorption at a ph below that which obtains during transfer image formation. Accordingly, the selected optical filter agent or agents should possess a pKa below that of the processing pH and above that of the environmental pH subsequent to transfer image formation.

As discussed previously, the concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. In the processes where the indicator dye or dyes selected as optical filter agents are used in conjunction with a reflecting agent or agents, the optical filter agents and reflecting agents together should possess the optical transmission density necessary to protect the photosensitive material for the particular photographic process. The optimum concentration of optical filter agent(s) or filter agent(s) together with reflecting agent(s) may be readily determined empirically for each photographic system.

While substantially any reflecting agent may be employed for the layer of reflecting agent, either preformed or applied as a component of the processing composition, it is preferred to select an agent that will not interfere with the color integrity of the dye transfer image, as viewed by the observer, and, most preferably, an agent which is aesthetically pleasing to the viewer and does not provide a background detracting from the information content of the image. Particularly desirable reflecting agents will be those providing a white background, for viewing the transfer image, and specifically those conventionally employed to provide background for reflection photographic prints and, especially, those agents possessing the optical properties desired for reflection of incident radiation.

As examples of reflecting agents, mention may be made of barium sulfate, zinc sulfide, titanium dioxide, barium stearate, silver flake, silicates, alumina, zirconium oxide, zirconium acetyl acetate, sodium zirconium sulfate, kaolin, mica, and the like.

Illustrative of the photographic use of the indicator dyes of the present invention as optical filter agents, a photographic film unit was prepared by coating, in succession, on a gelatin subbed, 4 mil. opaque polyethylene terephthalate film base, the following layers:

1. a layer of the cyan dye developer 1,4-bis-(β-[hydroquinonyl-α-methyl]-ethylamino)-5,8-dihydroxy-anthraquinone dispersed in gelatin and coated at a coverage of about 80 mgs./ft.$^2$ of dye and about 100 mgs./ft.$^2$ of gelatin;

2. a red-sensitive gelatino-silver iodobromide emulsion coated at a coverage of about 225 mgs./ft.$^2$ of silver and about 50 mgs./ft.$^2$ of gelatin;

3. a layer of the acrylic latex sold by Rohm and Haas Co., Philadelphia, Pa., U.S.A., under the trade designation AC-61 and polyacrylamide coated at a coverage of about 150 mgs./ft.$^2$ of AC-61 and about 5 mgs/ft.$^2$ of polyacrylamide;

4. a layer of the magenta dye developer 2-(p-[β-hydroquinonylethyl]-phenylazo)-4-isopropoxy-1-naphthol dispersed in gelatin and coated at a coverage of 70 mgs./ft.$^2$ of dye and about 120 mgs./ft.$^2$ of gelatin;

5. a green-sensitive gelatino-silver iodobromide emulsion coated at a coverage of about 120 mgs./ft.$^2$ of silver and 60 mgs./ft.$^2$ of gelatin;

6. a layer comprising the acrylic latex sold by Rohm and Haas Co. under the trade designation B-15 and polyacrylamide coated at a coverage of about 100 mgs./ft.$^2$ of B-15 and about 10 mgs./ft.$^2$ of polyacrylamide;

7. a layer of the yellow dye developer 4-(p-[β-hydroquinonylethyl]-phenylazo)-3-(N-n-hexyl-carboxamido)-1-phenyl-5-pyrazolone and the auxiliary developer 4'-methylphenyl hydroquinone dispersed in gelatin and coated at a coverage of about 50 mgs./ft.$^2$ of dye, about 15 mgs./ft.$^2$ of auxiliary developer and 50 mgs./ft.$^2$ of gelatin;

8. a blue-sensitive gelatino-silver iodobromide emulsion coated at a coverage of about 75 mgs./ft.$^2$ of silver and about 75 mgs./ft.$^2$ of gelatin; and 9. a layer of gelatin coated at a coverage of about 50 mgs./ft.$^2$ of gelatin.

Then a transparent 4 mil. polyethylene terephthalate film base was coated, in succession, with the following illustrative layers:

1. a 7:3 mixture, by weight, of polyethylene/maleic acid copolymer and polyvinyl alcohol at a coverage of about 1400 mgs./ft.$^2$, to provide a polymeric acid layer;

2. a graft copolymer of acrylamide and diacetone acrylamide on a polyvinyl alcohol backbone in a molar ratio of 1:3.2:1 at a coverage of about 800 mgs./ft.$^2$, to provide a polymeric spacer layer; and 3. a 2:1 mixture, by weight, of polyvinyl alcohol and poly-4-vinylpyridine, at a coverage of about 900 mgs./ft.$^2$ and including about 20 mgs./ft.$^2$ phenyl mercaptotetrazole, to provide a polymeric image-receiving layer.

The two components thus prepared were then taped together in laminate form, at their respective edges, by means of a pressure-sensitive binding tape extending around, in contact with, and over the edges of the resultant laminate.

A rupturable container comprising an outer layer of lead foil and an inner liner or layer of polyvinyl chloride retaining an aqueous alkaline processing solution comprising:

| | |
|---|---|
| Water | 100 cc. |
| Potassium hydroxide | 11.2 gms. |
| Hydroxyethyl cellulose (high viscosity) [commercially available from Hercules Powder Co., Wilmington, Delaware, under the trade name Natrasol 250] | 3.4 gms. |
| N-phenethyl-α-picolinium bromide | 2.7 gms. |
| Benzotriazole | 1.15 gms. |
| Titanium dioxide | 50.0 gms. |
| | 2.08 gms. |

2.08 gms.

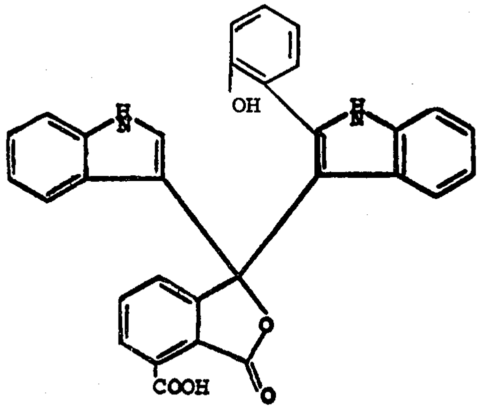

0.52 gms.

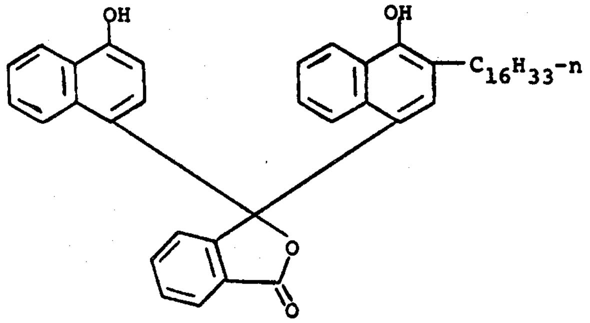

1.18 gms.

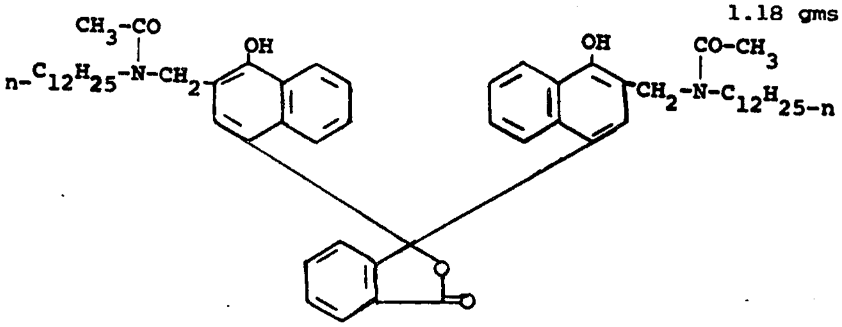

was then fixedly mounted on the leading edge of each of the laminates, by pressure-sensitive tapes interconnecting the respective containers and laminates, such that, upon application of compressive pressure to a container, its contents may be distributed, upon rupture of the container's marginal seal, between the polymeric image-receiving layer and next adjacent gelatin layer.

The photosensitive composite film units were exposed through step wedges to selectively filter radiation incident on the transparent polyethylene terephthalate layer and processed by passage of the exposed film units through appropriate pressure-applying members, such as suitably gapped, opposed rolls, to effect rupture of the container and distribution of its contents. During processing, the multicolor dye transfer image formation may be viewed through the transparent polyethylene terephthalate layer against the titanium dioxide background provided by distribution of the pigment containing processing composition between the polymeric image-receiving layer and gelatin layer 9 of the photosensitive component. The film unit may be exposed to incident light and the formation of the image may be viewed upon distribution of the processing composition by reason of the protection against incident radiation afforded the photosensitive silver halide emulsion layers by the optical filter agents and by reason of the effective reflective background afforded by the titanium dioxide.

The film unit detailed above is similar to that shown in FIG. 2 and related FIGS. 3 and 4 of aforementioned copending U.S. patent application Ser. No. 101,968 now U.S. Pat. No. 3,647,437. The negative component of the film unit including the photosensitive strata and associated dye-image-forming material; the positive component including the timing, neutralizing and dyeable layers; and the processing composition including its components, such as, the alkaline material and various addenda are described in detail in application Ser. No. 101,968 now U.S. Pat. No. 3,647,437. For convenience, the specification of this application is specifically incorporated herein.

Besides the above photosensitive element, the dyes of the present invention may be employed in composite photosensitive elements, in general, where the dyeable stratum along with any associated layers may be contained together with the photosensitive strata as a unitary film unit which may be termed an integral negative-positive film unit comprising a negative component including the aforementioned essential layers and a positive component including at least the dyeable stratum in which the color transfer image is to be formed. The essential layers are preferably contained on a transparent dimensionally stable layer or support member positioned closest to the dyeable stratum so that the resulting transfer image is viewable through this transparent layer. Most preferably another dimensionally stable layer which may be transparent or opaque is positioned on the opposed surface of the essential layers so that the aforementioned essential layers are sandwiched or confined between a pair of dimensionally stable layers or support members, at least one of which is transparent to permit viewing therethrough of a color transfer image obtained as a function of development of the exposed film unit in accordance with the known color diffusion transfer processes. It will be appreciated that all of these film units, like the specific one detailed above, may optionally contain other layers performing specific desired functions, e.g., spacer layers, pH-reducing layers, etc.

As examples of such integral negative-positive film units for preparing color transfer images viewable without separation are those described and claimed in aforementioned U.S. Pat. No. 3,415,644 and in U.S. Pat. Nos. 3,415,645, 3,415,646, 3,473,925, and 3,573,043; as well as those described in copending application Ser. No. 65,084, filed Aug. 19, 1970, now U.S. Pat. No. 3,672,890, in the name of Edwin H. Land; and Ser. Nos. 39,646 and 39,666 of Howard G. Rogers, filed May 22, 1970, now U.S. Pat. Nos. 3,594,165 and 3,594,164.

In general, the film units of the foregoing description, e.g., those described in the aforementioned patents and/or copending applications, are exposed to form a developable image and thereafter developed by applying the appropriate processing composition to develop exposed silver halide and to form, as a function of development, an imagewise distribution of diffusible dye image-providing material which is transferred, at least in part by diffusion, to the dyeable stratum to impart thereto the desired color transfer image, e.g., a positive color transfer image. Common to all of these systems is the provision of a reflecting layer between the dyeable stratum and the photosensitive strata to mask effectively the latter and to provide a background for viewing the color image contained in the dyeable stratum, whereby this image is viewable without separation, from the other layers or elements of the film unit. As discussed previously, this reflecting layer is provided prior to photoexposure, e.g., as a preformed layer included in the essential layers of the laminar structure comprising the film unit, and in others it is provided at some time thereafter, e.g., by including a suitable light-reflecting agent, for example, a white pigment, such as, titanium dioxide, in the processing composition. As an example of such a preformed layer, mention may be made of that disclosed in the copending applications of Edwin H. Land, Ser. Nos. 846,441, filed July 31, 1969, now U.S. Pat. No. 3,615,421 and 3,645, filed Jan. 19, 1970 now U.S. Pat. No. 3,620,724. The reflecting pigment may be generated in situ as is disclosed in the copending applications of Edwin H. Land, Ser. Nos. 43,741 and 43,742, both filed June 5, 1970 now U.S. Pat. Nos. 3,647,434 and 3,647,435, respectively. In a particularly preferred form, such film units are employed in conjunction with a rupturable container, such as, that used above, containing the processing composition having the light-reflecting agent incorporated therein which container is adapted upon application of pressure of distributing its contents to develop the exposed film unit and to provide the light-reflecting layer.

As noted previously, the photographic use of the dyes of the present invention as optical filter agents to prevent post-exposure fogging of a selectively exposed photosensitive material is not limited to diffusion transfer processes nor to such processes employing composite photosensitive elements. While the use of such dyes in composite multicolor diffusion transfer film units is a particularly preferred embodiment of the present invention, these dyes may be used with equally effective results in any photographic process where it is desired to protect a photosensitive material from incident radiation actinic to the photosensitive material within the wavelength range capable of being absorbed by the dye. For example, the subject dyes may be used in conventional tray photographic processing as a component of the processing bath, or they may be present in a layer coextensive with one or both surfaces of a layer of photosensitive material to be processed using conventional tray procedures, provided that they are non-light-absorbing prior to photoexposure and also subsequent to developing the latent image unless the layer containing the dye is to be removed subsequent to processing. In such procedures, the photoexposed photosensitive material will, of course, be transferred from the camera to the processing bath in the absence of radiation actinic to the material.

The subject dyes also may be employed in diffusion transfer processes where the photosensitive and image-receiving elements are separated subsequent to the formation of a transfer image or where a spreader sheet is separated from the photosensitive element to reveal a final image in the negative. In addition to the composite diffusion transfer structures described above, the subject dyes may be used with composite diffusion transfer film units where the final image is to be viewed by transmitted light. Also they may be used in composite film units specifically adapted, for example, for forming a silver transfer image, for developing a negative silver image by monobath processing, for obtaining an additive color image, and for obtaining a dye image by the silver dye bleach process which structures are described in detail in aforementioned copending U.S. application Ser. No. 101,968, now U.S. Pat. No. 3,647,437, particularly with reference to FIGS. 10 to 13 of the application's drawings.

In view of the foregoing, it will be readily apparent that the subject dyes are useful generally in photographic processes for producing silver, monochromatic and multi-color images using any photosensitive material including conventional and direct positive silver halide emulsions. Depending upon the selected photosensitive material, one or more of the dyes may be used alone or in combination with another optical filter agent, such as another light-absorbing dye, which second dye may be non-color-changing or another pH sensitive dye. If the selected dye or dyes do not possess the desired stability in the processing composition for long term storage therein, they may be initially disposed in the film structure or stored in a double-compartmented pod or in one of two associated pods separate from the processing solution until such time as the pod(s) are ruptured whereupon the dyes are admixed with the processing solution.

Since certain changes may be made in the above product and process without departing from the scope of the invention herein involved, it is intended that all matter contained in the above description shall be interpreted as illustrative and not in a limiting sense.

What is claimed is:

1. An indicator dye having the formula

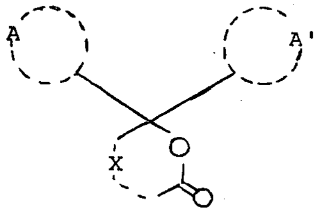

wherein A and A' are

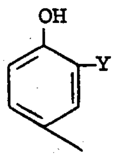 and 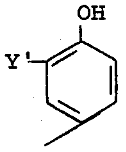 or

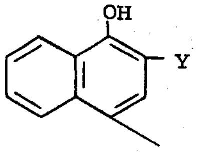 and 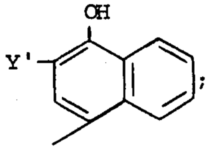;

Y is —$CH_2$—NRR' wherein R is hydrogen or acyl having the formula

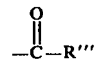

wherein R''' is alkyl having 1 to 20 carbon atoms, naphthyl, phenyl, phenylalkyl wherein said alkyl contains 1 to 12 carbon atoms and p-alkylphenyl wherein said p-alkyl has 1 to 12 carbon atoms and R' is a hydrocarbon group selected from alkyl having 1 to 20 carbon atoms, naphthyl, phenyl, phenylalkyl wherein said alkyl has 1 to 12 carbon atoms and p-alkylphenyl wherein said p-alkylcontains 1 to 12 carbon atoms; Y' is hydrogen or —$CH_2$—NRR' the same as Y; and X represents the atoms necessary to complete a ring-closing moiety selected from phthalide and naphthalide.

2. An indicator dye as defined in claim 1 wherein said dye is phthalide.

3. An indicator dye as defined in claim 1 wherein said A and A' are

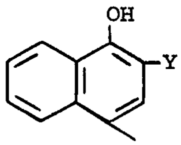 and 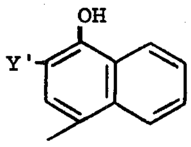.

4. An indicator dye as defined in claim 3 wherein said Y' is —$CH_2$—NRR' the same as Y.

5. An indicator dye as defined in claim 4 wherein R' is alkyl.

6. An indicator dye as defined in claim 5 wherein R is hydrogen.

7. An indicator dye as defined in claim 2 wherein said A and A' are

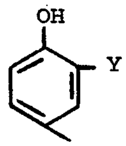 and 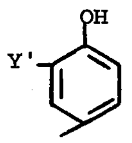.

8. An indicator dye as defined in claim 7 wherein said Y' is hydrogen.

9. An indicator dye as defined in claim 8 wherein R' is alkyl.

10. An indicator dye as defined in claim 9 wherein R is acyl.

11. An indicator dye as defined in claim 7 wherein said Y′ is $-CH_2-NRR'$ the same as Y.

12. An indicator dye as defined in claim 11 wherein R′ is alkyl.

13. An indicator dye as defined in claim 12 wherein R is hydrogen.

14. An indicator dye as defined in claim 12 wherein R is acyl.

15. An indicator dye as defined in claim 5 wherein R′ is n-dodecyl.

16. An indicator dye as defined in claim 15 wherein R is hydrogen.

17. An indicator dye as defined in claim 9 wherein R′ is n-dodecyl.

18. An indicator dye as defined in claim 17 wherein R is acetyl.

19. An indicator dye as defined in claim 12 wherein R′ is n-dodecyl.

20. An indicator dye as defined in claim 19 wherein R is hydrogen.

21. An indicator dye as defined in claim 19 wherein R is acetyl.

* * * * *